(12) United States Patent
Toyota et al.

(10) Patent No.: US 11,506,622 B2
(45) Date of Patent: Nov. 22, 2022

(54) GAS DETECTOR COMPRISING PLURAL GAS SENSORS AND GAS DETECTION METHOD THEREBY

(71) Applicant: Figaro Engineering Inc., Minoo (JP)

(72) Inventors: Masafumi Toyota, Minoo (JP); Kunihiko Maejima, Minoo (JP); Tomohiro Kawaguchi, Minoo (JP); Tatsuya Ishimoto, Minoo (JP)

(73) Assignee: FIGARO ENGINEERING INC., Osaka (JP)

(*) Notice: Subject to any disclaimer, the term of this patent is extended or adjusted under 35 U.S.C. 154(b) by 249 days.

(21) Appl. No.: 16/931,485

(22) Filed: Jul. 17, 2020

(65) Prior Publication Data
US 2021/0041386 A1 Feb. 11, 2021

(30) Foreign Application Priority Data

Aug. 8, 2019 (JP) ................. 2019-146119
Jan. 30, 2020 (JP) ............... JP2020-013471

(51) Int. Cl.
*G01N 27/12* (2006.01)
*G01N 33/00* (2006.01)
*G01M 3/40* (2006.01)

(52) U.S. Cl.
CPC ........... *G01N 27/123* (2013.01); *G01M 3/40* (2013.01); *G01N 27/12* (2013.01); *G01N 27/124* (2013.01); *G01N 33/0031* (2013.01); *G01N 33/0047* (2013.01); *G01N 33/0052* (2013.01); *G01N 27/128* (2013.01)

(58) Field of Classification Search
CPC .... G01N 27/123; G01N 27/12; G01N 27/124; G01N 33/0031; G01N 33/0047; G01N 33/0052; G01N 27/128; G01M 3/40
See application file for complete search history.

(56) References Cited

U.S. PATENT DOCUMENTS 4,423,407 A * 12/1983 Zuckerman ............ G01N 27/12
                                                    338/34
2002/0060150 A1* 5/2002 Hashimoto .......... G01N 33/007
                                                    205/784.5

FOREIGN PATENT DOCUMENTS

| EP | 3 153 849 A1 | 4/2017 |
| JP | 60-031049 A | 2/1985 |
| JP | 6288613 B2 | 3/2018 |

* cited by examiner

*Primary Examiner* — Benjamin R Schmitt
(74) *Attorney, Agent, or Firm* — Keating & Bennett, LLP

(57) ABSTRACT

A gas detector includes metal-oxide semiconductor gas sensors and their driving circuit. The gas detector stores the ratio of initial gas sensor resistance in air and that in an atmosphere including Freon gas, for the gas sensors. The gas detector learns sensor resistance in air for a gas sensor in use and detects Freon gas by comparing the sensor resistance of the gas sensor in use with the learned resistance in air divided by the ratio. When the first gas sensor has been used for a predetermined period, both the first gas sensor and a second gas sensor are used for a learning period to continue detection of Freon by the first gas sensor and to learn the resistance in air of the second gas sensor. After completion of the learning period, Freon is detected by the second gas sensor.

8 Claims, 9 Drawing Sheets

F I G. 11
FIG. 11A
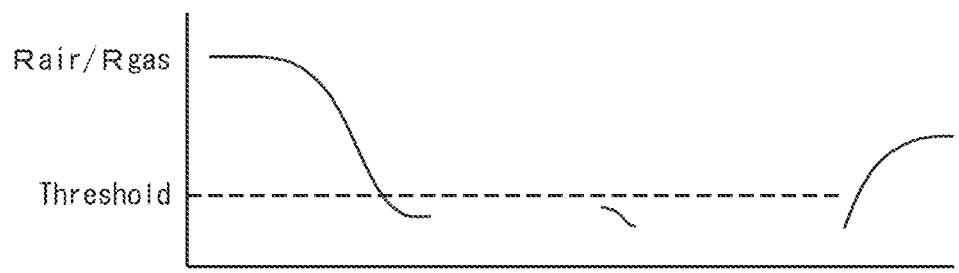
FIG. 11B
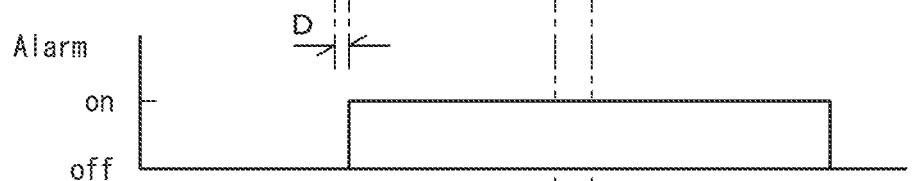
FIG. 11C

F I G. 12
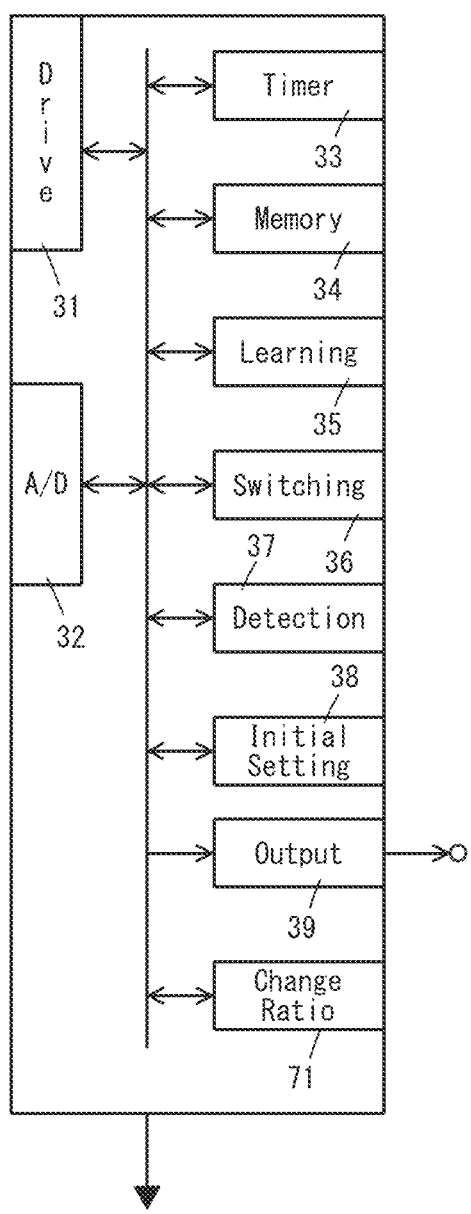

GAS DETECTOR COMPRISING PLURAL GAS SENSORS AND GAS DETECTION METHOD THEREBY

FIELD OF THE INVENTION

The invention relates to a gas detector comprising plural gas sensors and a gas detection method thereby.

BACKGROUND ART

There have been proposed gas detectors having plural gas sensors. For example, a gas detector proposed by JP S60-31049A has four gas sensors and uses them sequentially one by one. The detector counts the number of alarms for gas. The number of alarms indicates the frequency that a gas sensor in use has been exposed to gas, and therefore, when the number reaches a threshold, the gas sensor in use is deemed to be used up its service life. Therefore, a new gas sensor is used.

A gas detector proposed by JP 6288613B has plural gas sensors; one of them is heated and in use for detecting Freon gas leakage from a refrigerator or an air-conditioner, and others are preheated and in standby mode. When the gas sensor in use detects Freon gas, another gas sensor is made to be operated to confirm the Freon gas leakage.

A gas detector proposed by EP 3153849A has plural gas sensors for increasing the service life of the detector against poisoning compounds such as siloxanes. When one gas sensor has been used for a predetermined period, the gas sensor may be poisoned. Therefore, a next gas sensor is used for gas detection. Further, since the plural gas sensors can be integrated into one MEMS chip, the increase in the sensor cost can be reduced.

PRIOR DOCUMENT LIST

JP S60-31049A
JP 6288613B
EP 3153849A

SUMMARY OF THE INVENTION

The inventors have considered how to elongate the service life of a gas detector for detecting Freon gas, and so on. When detecting fron gas or similar gases, the resistances of gas sensors increase after several year's use. However, the inventors have found the ratio between the resistances in air and in an atmosphere including fron gas or a similar gas has been kept nearly constant for the period. Thus, the inventors have noticed that the service life of a gas detector can be elongated when detecting gas based upon the ratio between the resistances in air and in an atmosphere including fron gas or a similar gas. In this method, not the resistance of a gas sensor, but the ratio between the resistances is important. In this specification, gas detection upon the ratio Rair/Rgas between resistance in air Rair and resistance in gas Rgas is called "relative detection."

Providing plural gas sensors, and after using the first gas sensor for a predetermined period, the next gas sensor is used. If two gas sensors are used, then, the service life of the gas detector becomes about twice. However, according to relative detection, it is necessary to learn the resistance in air for a newly used sensor. Until the completion of the learning, the next gas sensor can not detect gas reliably.

Objects of the Invention

The objects of the invention are:
to expand the service life of a gas detector by using plural gas sensors sequentially and by using the relative detection; and
to maintain the reliability of gas detection when starting the use of a next gas sensor by adequately learning the resistance in air of the next gas sensor.

Solution

A gas detector according to the invention comprises: plural gas sensors provided with a metal-oxide semiconductor whose resistance changes based upon contact with a gas; and a driving circuit for operating the gas sensors.

The driving circuit comprises:
a timer means for counting the period that a gas sensor is operated;
a storage means for storing values S0 corresponding to the ratio Rair0/Rgas0 between initial resistance in air Rair0 of the metal-oxide semiconductor and initial resistance of the metal-oxide semiconductor in an atmosphere Rgas0 including a predetermined concentration of gas to be detected, for the plural gas sensors;
a learning means for learning resistance in air Rair of the metal-oxide semiconductor in a gas sensor being operated; and
a gas detection means for detecting occurrence of the gas to be detected when resistance Rs of the metal-oxide semiconductor of the gas sensor being operated becomes lower than a value Rgas/S0 corresponding to the learned resistance in air Rair divided by the ratio S0.

The driving circuit is configured and programmed to operate both a first gas sensor and a second gas sensor for a learning period, after the first gas sensor has been operated for a predetermined period, and to continue detection of the gas to be detected by the first gas sensor and to learn the resistance in air Rair of the metal-oxide semiconductor of the second gas sensor, both for the learning period; and to detect the gas to be detected by the second gas sensor, after completion of the learning period.

A gas detection method according to the invention uses a gas detector comprising: plural gas sensors provided with a metal-oxide semiconductor whose resistance changes based upon contact with a gas; and a driving circuit for operating the gas sensors.

The method comprises:
storing, by the driving circuit, values S0 corresponding to the ratio Rair0/Rgas0 between initial resistance in air Rair0 of the metal-oxide semiconductor and initial resistance Rgas0 of the metal-oxide semiconductor in an atmosphere including a predetermined concentration of gas to be detected, for the plural gas sensors;
learning, by the gas detector, resistance in air of the metal-oxide semiconductor in a gas sensor being operated;
detecting occurrence of the gas to be detected by the gas detector when resistance Rs of the metal-oxide semiconductor of the gas sensor being operated becomes lower than a value corresponding to the learned resistance in air Rair divided by the ratio S0;

counting the period that a gas sensor is operated by the driving circuit;

operating both a first gas sensor and a second gas sensor by the gas detector for a learning period, after the first gas sensor has been operated for a predetermined period, and to continue detection of the gas to be detected by the first gas sensor and to learn the resistance in air of the metal-oxide semiconductor of the second gas sensor, both for the learning period;

and detecting the gas to be detected by the gas detector using the second gas sensor, after completion of the learning period.

Even when the resistances Rs of gas sensors have drifted, in most cases, the ratio Rair/Rgas between the resistance in air Rair and the resistance in gas Rgas is kept nearly constant. Therefore, gas is detectable based upon a value corresponding to the resistance in air Rair learned by the learning means, divided by the above ratio S0 at an initial stage and the present and measured resistance Rs of the metal-oxide semiconductor. This expands the service life of a gas sensor.

Before operating the next gas sensor, the learning of the resistance in air Rair is needed. Therefore, the first and the second gas sensors are both operated to continue the detection of gas by the first gas sensor and also to learn the resistance in air Rair of the second gas sensor. Then, the second gas sensor can detect gas reliably.

Gas detectors that can be used for a long period without maintenance are needed for detecting leakage of refrigerant from air-conditioners and refrigerators. The gas detector according to the invention is reliably usable for fron gas (gases of chloro-fluoro-carbons, in particular, those of hydro-chloro-fluoro-carbons and hydro-fluoro-carbons) detection.

The gas sensors comprise: for example, a substrate; a metal-oxide semiconductor film whose resistance changes due to contact with gas; and a heater film, both deposited on the substrate. However, other gas sensors may be used. For example, a gas sensor comprising: a bead-like metal-oxide semiconductor; a heater, and at least an electrode, both embedded in the metal-oxide semiconductor, may be used. The decrease in reliability of gas sensors after long-term usage occurs regardless of the type of gas sensors.

Preferably, the learning period is down to one week and up to three months, for learning adequate resistance in air for the next gas sensor.

Preferably, the driving circuit is configured and programmed to add smaller electrical power to a heater of the second gas sensor than electrical power added to a heater of the first gas sensor when the first gas sensor is operated and the second gas sensor is in standby. The preheating reduces the accumulation of impurities such as adsorbed water and enhances the durability of the next gas sensor.

Preferably, the driving circuit is configured and programmed to operate a gas sensor being operated at a predetermined operational temperature, and when the gas sensor being operated detects fron gas having a concentration higher than a predetermined concentration, to output a leakage of fron gas to outside and to lower temperature of the gas sensor being operated from the predetermined operational temperature. Further preferably, the heater is made off, and the metal-oxide semiconductor is cooled to a temperature near from a room temperature. If the gas sensor is exposed to a high concentration of fron gas at the operation temperature, the characteristics of the metal-oxide semiconductor varies due to the combustion heat of the fron gas; for example, the resistance of the metal-oxide semiconductor increases. After outputting externally a leakage of fron gas, the next job for the gas sensor is to detect the decrease in the fron gas concentration. Since this job is not emergent, the temperature of the gas sensor is lowered, and the change in the characteristics is reduced.

Preferably, the driving circuit is configured and programmed to return intermittently the temperature of the gas sensor being operated to the predetermined operational temperature to detect whether the concentration of fron gas has decreased, after lowering the temperature of the gas sensor being operated. As a result, the reduction in the fron concentration is detectable.

Particularly preferably, the driving circuit is configured and programmed to detect leakage of fron gas based upon both decreasing rate of the resistance of the gas sensor being operated per unit time and the ratio Rari/Rs between the learned resistance in air Rair and resistance Rs of the gas sensor being operated. As a result, the leakage of fron gas is promptly detected before the resistance Rs of the gas sensor decreases enough. In addition, since the ratio Rair/Rgas between the learned resistance in air and resistance of the gas sensor is considered, the risk of mis-alarming due to cleaning solvents for air-conditioners or miscellaneous gasses is reduced.

BRIEF DESCRIPTION OF THE DRAWINGS

FIG. 6-(1) indicates the waveform of the detection voltage; and FIG. 6-(2) indicates the sampling of the output voltage.

FIG. 11 is a waveform diagram indicating the operation of the gas detector according to the modification: FIG. 11-(A) indicates the resistance of the gas sensor; FIG. 11-(B) indicates the on/off of alarm (external output) ; and FIG. 11-C) indicates the heater power to the gas sensor.

FIG. 12 is a block diagram in part of a gas detector according to a second modification.

Embodiment

The best embodiments and its modifications will be described.

Figure 1:
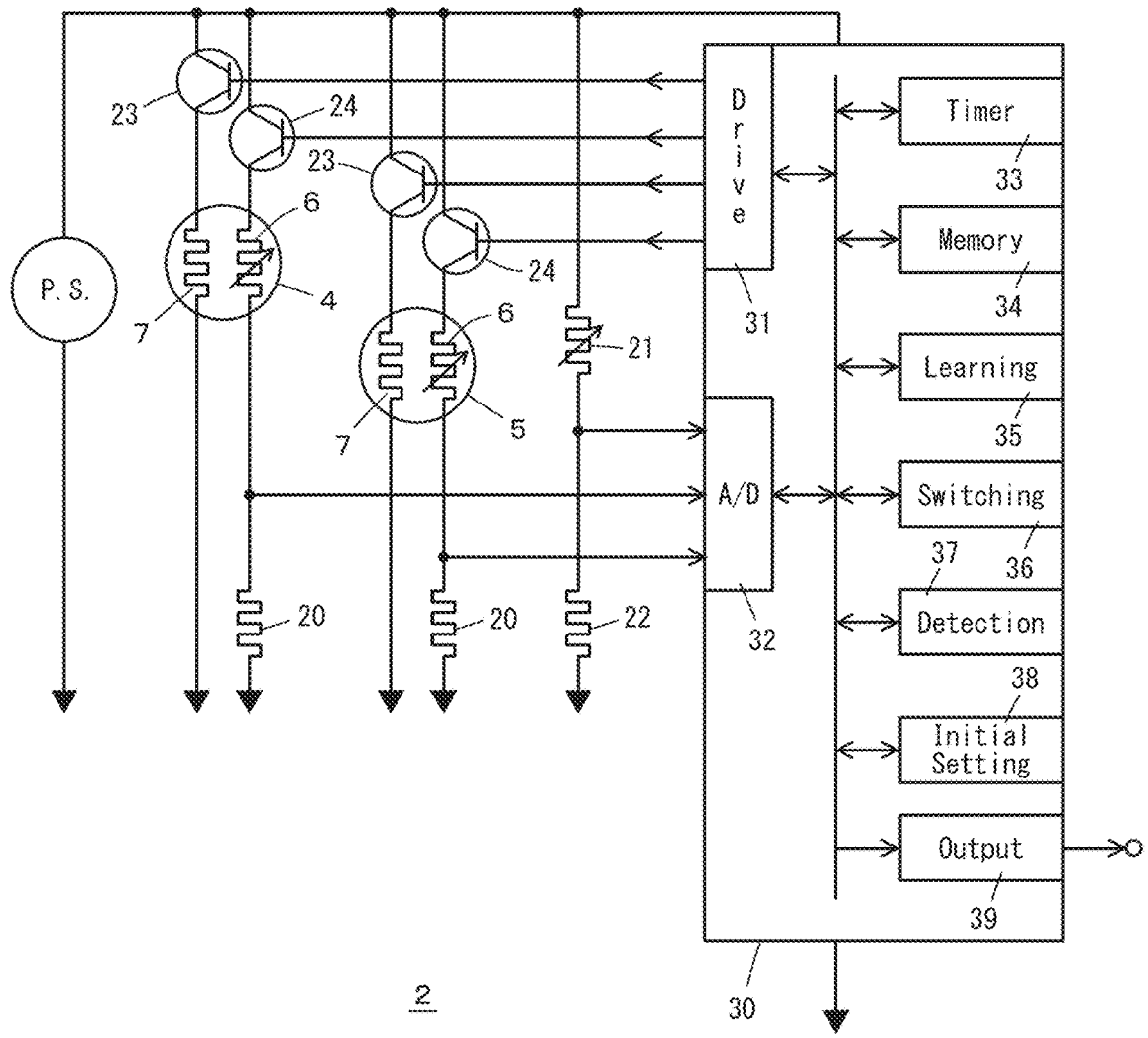
FIG. 1 is a block diagram of a gas detector according to the best embodiment.

FIGS. 1 to 7 indicate the best embodiment. FIG. 1 indicates the structure of the gas detector 2; the gas detector 2 includes two metal-oxide semiconductor gas sensors 4 and 5, and they are of the same type and for the detection of, for example, fron gas, such as slightly flammable R32 (CH2F2). Other than fron gas, VOC (volatile organic compounds) in air, gases from living bodies such as acetone or ethanol from human bodies, and so on, may be detected, and arbitrary gases can be detected. The embodiment is suitable for the relative detection of gases; the resistance in air Rair of the metal-oxide semiconductor in the gas sensors 4, 5 is learned and the gases are detected according to the ratio S0 between the resistance Rs of the metal-oxide semiconductor and the learned resistance in air Rair. The gas sensor 4 is the first gas sensor to be used first and the gas sensor 5 is the second gas sensor to be used next; the third and the fourth gas sensors and so on may be provided.

Figure 2:
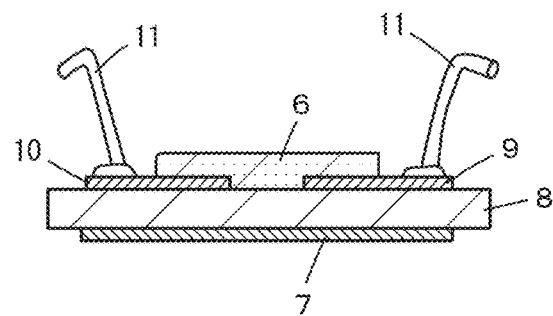
FIG. 2 is a partial sectional view of a gas sensor used in the embodiment.
Figure 3:
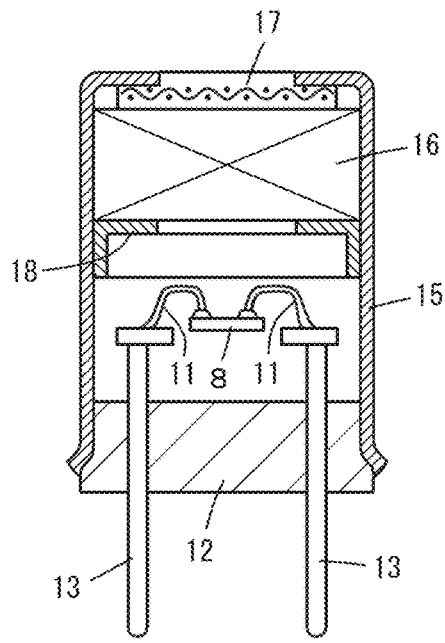
FIG. 3 is a total sectional view of the gas sensor used in the embodiment.

FIGS. 2 and 3 depict the structure of the gas sensors 4, 5. A metal-oxide semiconductor film 6 and a heater film 7 are supported on a substrate 8, and to the metal-oxide semiconductor film 6, for example, a pair of electrodes 9, 10 are connected. Onto pads on the substrate 8 (not shown), four leads 11 are connected. The metal-oxide semiconductor film 6 is, for example a thick film of SnO2, but the materials and the thickness of the metal-oxide semiconductor film 6 are arbitrary. The resistance of the metal-oxide semiconductor film 6 decreases when in contact with flammable gases such as fron gas. The operational temperature of the metal-oxide semiconductor film 6 for the detection of gases is for example about 400 degree Celsius and is determined according to the gases to be detected. The gas sensor 5 that is kept in standby before use may be kept at room temperature, but preferably, the metal-oxide semiconductor film 6 is heated at an intermediate temperature between the operational temperature and room temperature, for example at 100 degree Celsius or the like.

The leads 11 are connected to pins 13 fixed to a base 12. The surrounding of the substrate 8 is covered by a cap 15, and the atmosphere is introduced towards the substrate 8, from an opening in the cap 15, for example at the top of the cap 15, and through the filter 16. By the way, indicated by 17 is a metal mesh and by 18 is a support ring for the filter 16. The filter 16 comprises for example zeolite that reduces poisoning materials such as siloxanes to the metal-oxide semiconductor film 6 and also reduces gases such as ethanol that interfere with the detection of fron gas. The type and the structure of the gas sensors 4, 5 are arbitrary. For example, on an insulating film covering a cavity in a silicon chip, the metal-oxide semiconductor film 6, the electrode films 9, 10, and the heater film 10 may be provided such that they form a MEMS gas sensor. In addition, the heater film 7 may be used also as the electrode, and the parallel resistance of the metal-oxide semiconductor film 6 and the heater film 7 may be detected. In this case, the electrodes 9, 10 are not needed.

The gas sensors 4, 5 have a problem that the resistance of the metal-oxide semiconductor film 6 increases when kept at a high temperature for a long period. For example, when used continuously for seven years, it has been observed that the resistance of the metal-oxide semiconductor film 6 in air and also that in fron gas have increased up to about 10 times of the initial values in air and in fron gas. However, the ratio Rair/Rgas of the resistance in air Rair, and that in gas Rgas, is found to be kept nearly constant when the resistance Rs of the metal-oxide semiconductor film 6 has increased. Therefore, nearly accurate detection of fron gas is performed by:

learning the resistance in air Rair of the metal-oxide semiconductor film 6;

storing the initial ratio Rair0/Rgas0 between the resistance in air Rair, and that in fron gas Rgas; and comparing the measured resistance Rs of the metal-oxide semiconductor 6 with a quotient of the learned resistance in air Rair, divided by the stored ratio Rair0/Rgas0 of the initial resistance in air, Rs and that in a predetermined concentration of fron gas Rgas. Since the ratio Rair/Rgas of the resistance in air Rair, and the resistance in gas Rgas is kept constant, this algorithm affords nearly accurate gas detection.

By the way, as the signal, for example, the resistance of the metal-oxide semiconductor film 6 is used, but other signals corresponding to the resistance of the metal-oxide semiconductor film 6 are usable. For example, the electrical conductivity, namely the inverse of the resistance, voltage to the load resistors of the gas sensors 4, 5, or powers of the electrical conductivity that is linear to the gas concentration may be used. Further, instead of the ratio Rair/Rgas, the ratio between the resistance in air Rair, and the resistance Rgas in a predetermined concentration of fron gas, its inverse Rgas/Rair is usable. Namely, the detection is performed according to the following two factors: One corresponds to the learned resistance in air Rair, divided by the resistance ratio Rair0/Rgas0 (S0) of the initial resistance in air Rair0, and the initial resistance in a predetermined concentration of fron gas Rgas0; and the other corresponds to the measured present resistance Rs of the metal-oxide semiconductor film 6. The processing circuit in the gas detector 2 may process the resistance, the electric conductivity, or other signals and may use, as the initial gas sensitivity S0, the ratio Rair0/Rgas0 between the resistance in air and that in Freon gas, or another parameter.

After the first gas sensor 4 will have been used for 7.5 years, the next gas sensor 5 will be used. The next gas sensor 5 is constantly preheated for example at 100 degree Celsius in standby mode; this preheating reduces the long term drift in the resistance of the metal-oxide semiconductor film 6 due to the accumulation of adsorbed water or the like. Therefore, during the period when the first gas sensor 4 is operated, it is preferable to preheat the nest gas sensor 5.

Returning now to FIG. 1, a power supply P.S. supplies electricity to the gas detector 2, and the gas sensors 4, 5 are connected to load resistors 20, 20. For temperature compensation, a temperature sensor, such as thermistor 21 is connected to a load resistor 22. Switches 23, 24 such as transistors are connected to the heater film 7 and to the metal-oxide semiconductor film 6 of the gas sensors 4, 5 to drive the gas sensors 4, 5. The switches 24 may be connected to the load resistors 20. A microcomputer 30 controls the gas detector 2 and is the major portion of the driving circuit of the gas detector 2.

The microcomputer 30 will be described. A driver 31 drives the switches 23, 24 so that initially the first gas sensors 4 is driven for the first 7.5 years, and then, the next gas sensor 5 will be driven. The switches 23 control the heater power to the heater films 7 for example, by PWM (pulse width modulation) control to heat the metal-oxide semiconductor films 6 to an operational temperature. Further, the switches 24 add pulsively a detection voltage with a short duration to the metal-oxide semiconductor films 6.

An A/D converter 32 converts the voltage to the load resistors 20, 20, 22, and so on, to digital signals. A timer 33 counts the clock signal or a similar signal in the microcomputer 30: to calculate the period of the gas sensors 4, 5 in use; to count the learning period of the resistance in air Rair of the gas sensor 5 when changing the gas sensor in use from the from gas sensor 4 to the next gas sensor 5; to generate the on/off signals for the switches 23, 24; and to perform similar jobs. A memory 34 stores the initial sensitivities S0 for each of the gas sensors 4, 5; the initial sensitivity S0 is the ratios of the initial resistance in air Rair07 and the initial resistance in a predetermined concentration of fron gas Rgas0. According to the embodiment, the memory 34 further stores the initial resistance in air Rair0. Since the resistance Rs of the metal-oxide semiconductor films 6 is dependent upon ambient temperature, it is preferable that the microcomputer 30 corrects the measured resistance according to the signal of the thermistor 21 and uses the corrected resistance in the microcomputer 30.

The microcomputer 30 learns the resistance in air Rair of the gas sensors 4, 5 according to a learning algorithm. According to the embodiment, the microcomputer 30 learns the moving average of the resistance in air Rair for preceding 30 days and in particular, learns the moving average for 30 days of the maximum resistance of the gas sensors 4, 5 in one day. In the specification, the resistance of the gas sensors 4, 5 means that of the metal-oxide semiconductor film 6. Instead of the moving average, the modal value or the median value of the resistance distribution over a period such as 30 days may be learned. Since the air quality where the gas sensors 4, 5 are placed is expected to change with a period of 1 day, the maximum resistance in 1 day is expected to correspond to the resistance in the cleanest air in 1 day and therefore is measured. Since the air quality is expected to change with a period of 1 day as stated above, the learning needs plural days, preferably at least 1 week and up to 3 months, and therefore, learning during 30 days is performed according to the embodiment.

The microcomputer 30 changes the gas sensor in use from the first gas sensor 4 to the next gas sensor 5 according to switching algorithm 36 when the gas detector 2 has been used for 7.5 years or when the resistance in air Rair of the gas sensor 4 has become 10 times or more of the initial resistance in air Rair0. When changing the gas sensor, the first gas sensor 4 is still used for the detection of fron gas during the learning period of 30 days, and the resistance in air Rair of the next gas sensor 5 is learned for this period. Then, the first gas sensor 4 is halted, and the next gas sensor 5 will be used for the detection of fron gas.

The microcomputer 30 performs the setup of the initial sensitivity S0, and the setup of the initial resistance in air Rair0, according to the initial setup algorithm 38, and the setup values are stored in the memory 34. The microcomputer 30 detects the occurrence of fron gas according to detection algorithm 37. The learned resistance in air Rair is divided by the initial sensitivity S0, and the ratio between these values, Rair/S0 is used as a threshold. The threshold Rair/S0 is compared with the measured present resistance Rs of the gas sensors 4, 5, and if the resistance Rs is under or equal to the threshold, Rair/S0, then, an output signal (alarm signal) is outputted via an output interface 39.

Figure 4:
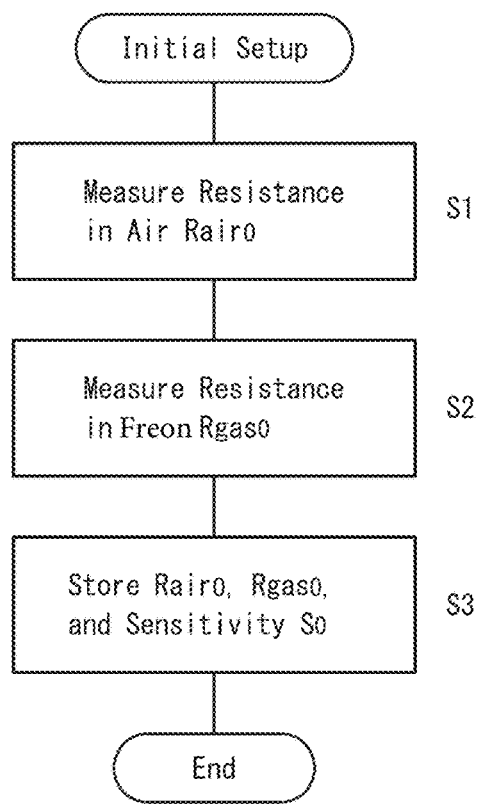
FIG. 4 is a flowchart indicating the initial setup algorithm according to the embodiment.

FIGS. 4 to 7 indicate the operation of the gas detector 2. FIG. 4 indicates the initial setup algorithm. In step S1, the resistances in air Rair0 are measured regarding both the gas sensors 4 and 5, and in step S2, the resistances in a predetermined concentration of fron gas Rgas0 are measured regarding both the gas sensors 4 and 5. In step S3, the initial sensitivities S0, namely the ratio Rair0/Rgas0 between the resistance in air Rair0, and the resistance in the fron gas Rgas0, are stored regarding both the gas sensors 4 and 5.

Figure 5:
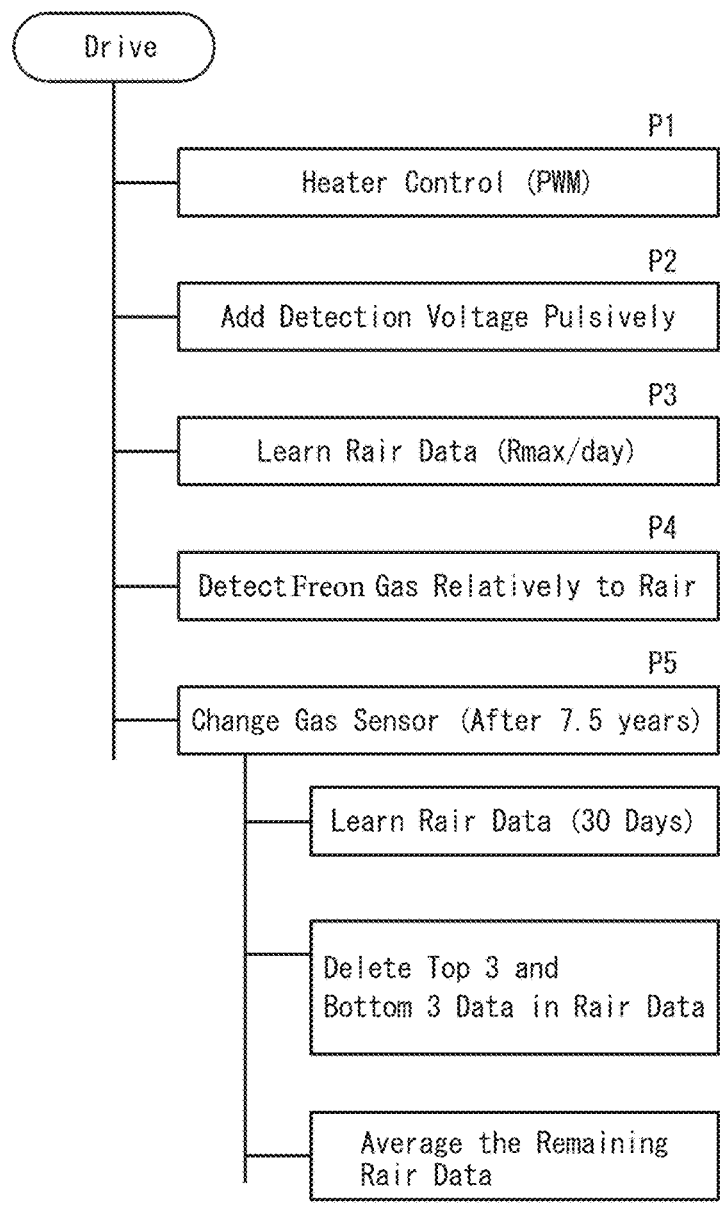
FIG. 5 is a flowchart indicating the operational algorithm of the gas detector according to the embodiment.
Figure 6:
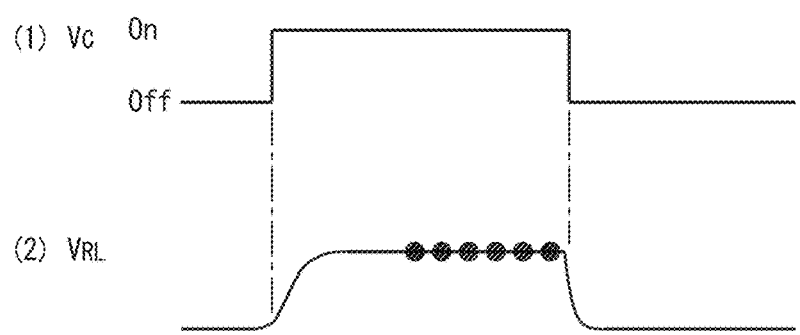
FIG. 6 is a waveform diagram indicating the sampling of the resistance of the metal-oxide semiconductor according to the embodiment.
Figure 7:
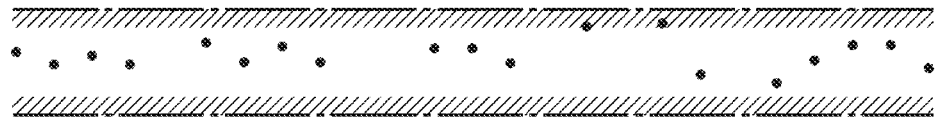
FIG. 7 indicates the sampling of the resistance in air according to the embodiment.

FIG. 5 indicates the overall operation algorithm of the gas detector 2. In process P1, the heater film 7 of the gas sensor in use is for example PWM controlled, while the heater film 7 of the gas sensor in standby mode is for example PWM controlled with a smaller duty ratio than the gas sensor in use for preheating. In process P2, detection voltage is applied pulsively to the metal-oxide semiconductor film 6 of the gas sensor in use and its load resistor 20. FIG. 6-(1) indicates the waveform of the detection voltage, and, for example, the detection voltage Vc with a time duration of 2 msec is applied once per second. As is shown in FIG. 6-(2), during the latter half of the period when the detection voltage Vc is applied, the voltage to the load resistor 20 is converted into digital values for example, 7 times. After extruding the maximum and minimum values from the converted values, the average of the remaining 5 values is calculated. This average is corrected according to the temperature measured by the thermistor 21 to temperature compensated resistance of the metal-oxide semiconductor film 6. This temperature compensated resistance is used as the resistance Rs in the embodiment.

In process P3, the resistance in air Rair is learned, and for this purpose, the maximum resistance of the metal-oxide semiconductor film 6 in one day is stored for the preceding 30 days. The dots in FIG. 7 indicate these maximum resistances, the top three data and the bottom three data are excluded, and the average of the remaining 24 data is calculated. This average of the 24 data is compared with the value stored as the resistance in air Rair, and when the difference is within plus-minus 3%, the average of the 24 data is stored as the new resistance in air Rair. When the difference is larger than plus-minus 3%, then the value stored as the resistance in air Rair is changed by plus-minus 3% towards the average. The learning method of the resistance in air Rair is arbitrary. The preferable condition is that data at least for one week and utmost for three months is reflected and that the resistance in air Rair is changed gradually.

In process P4, when the resistance of the metal-oxide semiconductor film 6 becomes equal to or lower than the ratio Rair/S0 between the learned resistance in air Rair and the initial sensitivity S0, the occurrence of fron gas is detected. In most cases, it is due to the leak of refrigerant from an air-conditioner or a refrigerator.

In process P5, the switching from the first gas sensor 4 to the next gas sensor 5 is performed. The learning period is for example 30 days, in this period, the detection of fron gas is performed by the first gas sensor 4, and the resistance in air Rair is learned for the next gas sensor 5, similarly as process P3. From the 30 days data, the top three data and the bottom three data are excluded, and the average of the remaining 24 data is stored as the resistance in air Rair for the next gas sensor 5.

After the learning period, the first gas sensor 4 is for example halted, the gas detection will be performed by the next gas sensor 5, and the learning of the resistance in air Rair for the next gas sensor 5 will be performed. When the gas detector 2 will be used for 15 years, the expiration of the service life of the gas detector 2 will be outputted.

Modifications of Gas Sensors

Figure 8:
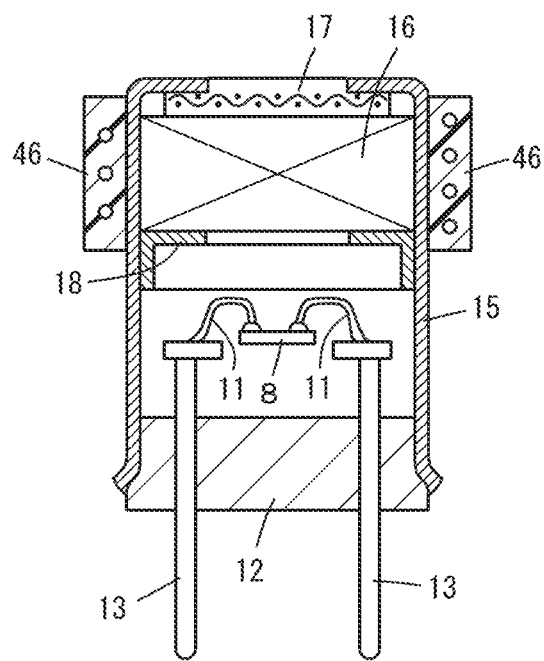
FIG. 8 is a sectional view of a modified gas sensor.
Figure 9:
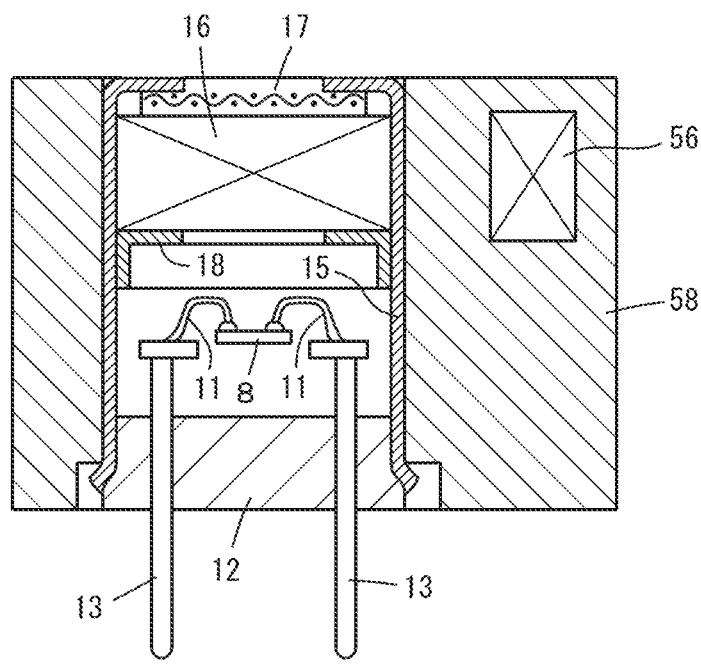
FIG. 9 is a sectional view of another modified gas sensor.

FIGS. 8 and 9 indicate gas sensors 45 and 55 to be used next, according to modifications. When the gas sensor is in standby, the filter 16 may accumulate poisoning gases such as siloxanes, fron gas, or organic solvents. When the gas sensor will be used, these gases may desorb from the filter 16 due to the heat from the heater film 7 of the gas sensor. If the desorbed gases will contact the metal-oxide semiconductor film 6, the signal from the gas sensor may become unstable. Therefore, it is preferable to heat the filter 16 for example to 50 to 150 degree Celsius continuously when in standby mode, so as to reduce the adsorption of gases such as siloxanes to the filter 16. Or it is preferable to preheat the filter 16 of the gas sensors 45, 55 to be used next for example at 100 to 200 degree Celsius for one hour to one day, before the gas sensors 45, 55 will be used. After the filter 16 is cleaned and the adsorbed gases such as siloxanes are enough desorbed, the operation of the next gas sensors 45, 55 is started similarly as the embodiment. Regarding other points, the embodiment similarly applies.

The gas sensor 45 shown in FIG. 8 has a ring-like heater 46 provided around the periphery of the cap 15 (a heat-resistant cap comprising metal or ceramic in the modification) of the gas sensor 45 such that the heater 46 surrounds the filter 16. The heater 46 comprises, for example, a ring of heat-resistant plastic and a wire winded and fixed in the ring.

The gas sensor 55 shown in FIG. 9 has a metal block 58 made of aluminum or the like with a heater 56 in it and surrounding the gas sensor. Here the cap 15 of the gas sensor 55 is made of metal or ceramic and therefore heat-resistant. The heat from the heater 56 heats the entire gas sensor 55 and heats both the filter 16 and the substrate 8.

Modification 1

Figure 10:
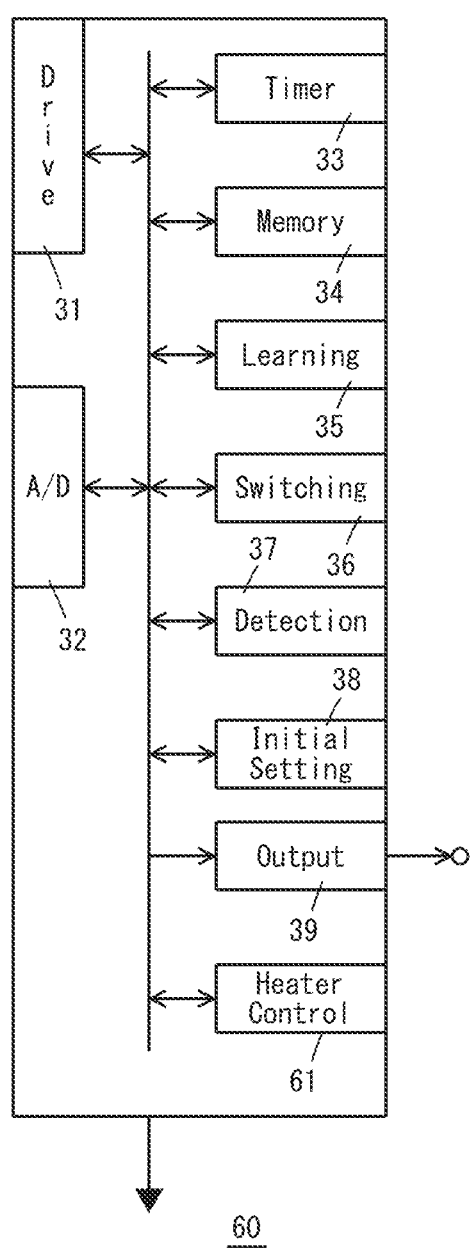
FIG. 10 is a block diagram in part of a gas detector according to a first modification.

FIGS. 10, 11 indicate a first modification where the heater in the gas sensors 4 and 5 are halted when fron gas occurrence above the alarm concentration is detected. The alarm concentration is one that needs an external alarm, for example, 5000 ppm fron. A microcomputer 60 is provided newly with heater control algorithm 61 and when fron gas above the alarm concentration is detected, the heater of the gas sensor in use is halted. In other points, the microcomputer 60 is the same as the microcomputer 30 in FIG. 1.

As shown in FIG. 11 (A), the resistance of the gas sensor in use (the resistance of the metal-oxide semiconductor film 6) decreases under the alarm threshold, it is reported outside after a delay time D. Then, the heater of the gas sensor is halted and then is re-heated for 30 seconds for every 5 minutes for example, (FIG. 11 (C)) so as to check whether the resistance of the gas sensor has been recovered (FIG. 11 (A)). When the resistance is kept low, the heater is halted once more, and it is checked whether the resistance is recovered (FIG. 11 (C)). When the resistance of the gas sensor is recovered above a predetermined value, then, the gas sensor is operated at the normal operation temperature.

This modification prevents that the resistance of the metal-oxide semiconductor film 6 varies due to contact with fron gas of high concentration. The heater may not be halted but the heater power may be reduced such that the temperature of the metal-oxide semiconductor film 6 lowers for example by 100 degree Celsius or more, preferably by 200 degree Celsius or more.

Modification 2

Figure 13:
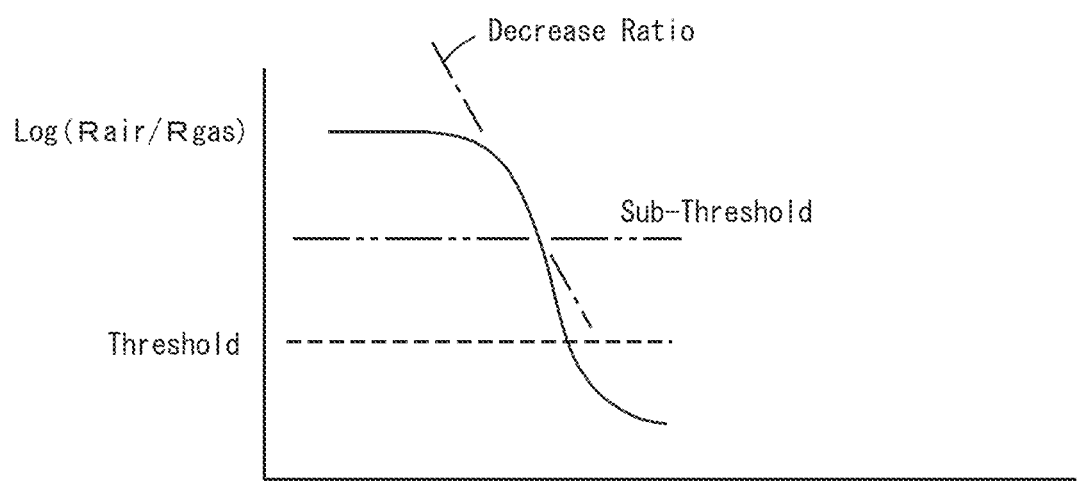
FIG. 13 is a diagram indicating the gas detection mechanism according to the second modification.

FIGS. 12 and 13 indicate a second modification that detects the leak of fron gas based upon the decreasing rate of the resistance of the metal-oxide semiconductor film 6. In this modification, the output of the gas sensors 4, 5 is the ratio Rair/Rgas of the learned resistance in air Rair, and the measured present resistance Rgas. In the specification, Rs and Rgas mean a present measured value of the resistance of the metal-oxide semiconductor film 6. Using the logarithm of Rair/Rgas, the decreasing rate of the gas sensor output can be calculated; the sign of positive/negative of the decreasing rate is neglected in the following description. When the decreasing rate is constantly equal to or over a predetermined value for a period such as 10 seconds or more, and when the output of the gas sensor indicates that the fron concentration is equal to or over an auxiliary threshold such as 3000 ppm fron, it is plausible that fron leakage is in progress. Here the auxiliary threshold is lower than the alarm threshold in fron concentration. When the above conditions are satisfied, an alarm is outputted. Thus, before the fron concentration reaches the alarm threshold of 5000 ppm, the fron leakage can be detected.

The new microcomputer 70 is provided with a detection algorithm of decreasing rate 71 and detects the changing rate in the logarithm of Rair/Rgas for example. This change can be detectable by simply detecting the differences or detecting smoothed differences between measured resistances Rgas. In other points, the microcomputer 70 is the same as the microcomputer 30 in FIG. 1.

DESCRIPTION OF SYMBOLS 2 gas detector
4, 5 gas sensors
6 metal-oxide semiconductor film
7 heater film
8 substrate
9, 10 electrodes
11 leads
12 base
13 pin
15 cap
16 filter
17 metal mesh
18 support ring
20, 22 load resistors
21 thermistor
23, 24 switches
30 microcomputer
31 driver
32 A/D converter
33 timer
34 memory
35 learning algorithm
36 switching algorithm
37 detection algorithm
38 initial setup algorithm
39 output interface
45, 55 gas sensors
46, 56 heaters
58 metal block
60 microcomputer
61 heater control algorithm
70 microcomputer
71 detection algorithm of decreasing rate
D delay time.

What is claimed is:

1. A gas detector comprising: plural gas sensors provided with a metal-oxide semiconductor whose resistance changes based upon contact with a gas; and a driving circuit for operating the gas sensors wherein the driving circuit comprises:

a timer means for counting the period that a gas sensor is operated;

a storage means for storing values corresponding to the ratio between initial resistance in air of said metal-oxide semiconductor and initial resistance of said metal-oxide semiconductor in an atmosphere including a predetermined concentration of gas to be detected, for the plural gas sensors;

a learning means for learning resistance in air of said metal-oxide semiconductor in a gas sensor being operated; and a gas detection means for detecting occurrence of the gas to be detected when resistance of the metal-oxide semiconductor of the gas sensor being operated becomes lower than a value corresponding to the learned resistance in air divided by said ratio;

wherein said driving circuit is configured and programmed to operate both a first gas sensor and a second gas sensor for a learning period, after the first gas sensor has been operated for a predetermined period, and to continue detection of the gas to be detected by the first gas sensor and to learn the resistance in air of the metal-oxide semiconductor of the second gas sensor, both for the learning period; and wherein said driving circuit is configured and programmed to detect the gas to be detected by the second gas sensor, after completion of the learning period.

2. The gas detector according to claim 1, wherein the gas to be detected is Freon gas (chloro-fluoro-carbon gas).

3. The gas detector according to claim 2, wherein the learning period is between one week and three months.

4. The gas detector according to claim 2, wherein the driving circuit is configured and programmed to add smaller electrical power to a heater of the second gas sensor than electrical power added to a heater of the first gas sensor when the first gas sensor is operated and the second gas sensor is in standby.

5. The gas detector according to claim 2, wherein the driving circuit is configured and programmed to operate a gas sensor being operated at a predetermined operational temperature, and when the gas sensor being operated detects Freon gas having a concentration higher than a predetermined concentration, to output a leakage of Freon gas to outside and to lower temperature of the gas sensor being operated from the predetermined operational temperature.

6. The gas detector according to claim 5, wherein the driving circuit is configured and programmed to return intermittently the temperature of the gas sensor being operated to the predetermined operational temperature to detect whether the concentration of Freon gas has decreased, after lowering the temperature of the gas sensor being operated.

7. The gas detector according to claim 2, wherein the driving circuit is configured and programmed to detect leakage of Freon gas based upon both decreasing rate of the resistance of the gas sensor being operated per unit time and the ratio between the learned resistance in air and resistance of the gas sensor being operated.

8. A gas detection method using a gas detector comprising: plural gas sensors provided with a metal-oxide semiconductor whose resistance changes based upon contact with a gas; and a driving circuit for operating the gas sensors, said method comprising:

storing, by the driving circuit, values corresponding to the ratio between initial resistance in air of said metal-oxide semiconductor and initial resistance of said metal-oxide semiconductor in an atmosphere including a predetermined concentration of gas to be detected, for the plural gas sensors;

learning, by the gas detector, resistance in air of said metal-oxide semiconductor in a gas sensor being operated;

detecting occurrence of the gas to be detected by the gas detector when resistance of the metal-oxide semiconductor of the gas sensor being operated becomes lower than a value corresponding to the learned resistance in air divided by said ratio;

counting the period that a gas sensor is operated by the driving circuit;

operating both a first gas sensor and a second gas sensor by the gas detector for a learning period, after the first gas sensor has been operated for a predetermined period, and to continue detection of the gas to be detected by the first gas sensor and to learn the resistance in air of the metal-oxide semiconductor of the second gas sensor, both for the learning period; and detecting the gas to be detected by the gas detector using the second gas sensor, after completion of the learning period.

\* \* \* \* \*